(12) United States Patent
Dauga

(10) Patent No.: US 7,127,280 B2
(45) Date of Patent: Oct. 24, 2006

(54) APPARATUS AND PROCESS FOR EXAMINING A SURFACE

(75) Inventor: Christophe Dauga, Levallois-Perret (FR)

(73) Assignee: L'Oreal, Paris (FR)

( * ) Notice: Subject to any disclaimer, the term of this patent is extended or adjusted under 35 U.S.C. 154(b) by 431 days.

(21) Appl. No.: 09/886,395

(22) Filed: Jun. 22, 2001

(65) Prior Publication Data
US 2002/0087085 A1    Jul. 4, 2002

(30) Foreign Application Priority Data
Jun. 23, 2000   (FR) .................................. 00 08093

(51) Int. Cl.
    *A61B 5/00*   (2006.01)
(52) U.S. Cl. .................... 600/407; 600/476; 356/369; 356/445; 356/600; 382/108
(58) Field of Classification Search ............... 600/476, 600/407; 356/342, 376, 364, 369, 445, 600; 382/108
See application file for complete search history.

(56) References Cited

U.S. PATENT DOCUMENTS

| | | | | |
|---|---|---|---|---|
| 5,198,875 | A * | 3/1993 | Bazin et al. ............. | 356/369 |
| 5,247,344 | A * | 9/1993 | Doan ..................... | 356/394 |
| 5,408,998 | A * | 4/1995 | Mersch | |
| 5,552,890 | A * | 9/1996 | Nanna et al. ............. | 356/369 |
| 5,557,324 | A * | 9/1996 | Wolff .................... | 345/207 |
| 5,636,637 | A * | 6/1997 | Guiolet et al. ............ | 600/476 |
| 5,841,538 | A * | 11/1998 | Schoeffler et al. ......... | 356/369 |
| 5,847,394 | A * | 12/1998 | Alfano et al. ............. | 250/341.8 |
| 5,974,160 | A * | 10/1999 | Shiratori et al. .......... | 382/112 |
| 6,011,626 | A * | 1/2000 | Hielscher et al. .......... | 356/367 |
| 6,024,449 | A * | 2/2000 | Smith ..................... | 351/212 |
| 6,032,071 | A | 2/2000 | Binder | |
| 6,046,811 | A * | 4/2000 | Wolff et al. .............. | 356/369 |
| 6,081,612 | A * | 6/2000 | Gutkowicz-Krusin et al. ..................... | 382/128 |
| 6,177,984 | B1 * | 1/2001 | Jacques .................. | 356/39 |
| 6,280,386 | B1 * | 8/2001 | Alfano et al. ............. | 600/431 |
| 6,804,003 | B1 * | 10/2004 | Wang et al. .............. | 356/369 |

FOREIGN PATENT DOCUMENTS

| | | |
|---|---|---|
| EP | 0475803 A1 | 8/1991 |
| EP | 0726456 A1 | 8/1996 |
| FR | 2650890 | 2/1991 |
| JP | 58018146 A | 2/1983 |
| JP | 02129503 A | 5/1990 |
| JP | 02304336 A | 12/1990 |
| JP | 05256795 A | 10/1993 |
| WO | WO99/37980 | 7/1999 |

OTHER PUBLICATIONS

Wolff et al., "Liquid Crystal Polarization Camera," *IEEE Transactions on Robotics and Automation*, vol. 13, No. 2, Apr. 1997, pp. 195-220.

* cited by examiner

*Primary Examiner*—Ruth S. Smith
(74) *Attorney, Agent, or Firm*—Pillsbury Winthrop Shaw Pittman LLP

(57) ABSTRACT

An apparatus designed to examine a surface includes a polarization analyser element, or analyser, placed in the path of a light beam reflected by the surface, a device configured to take digital images and placed in the path of the beam reflected by the surface downstream of the analyser, and a processing unit capable of calculating the color and the intensity of a plurality of pixels of at least one image.

23 Claims, 4 Drawing Sheets

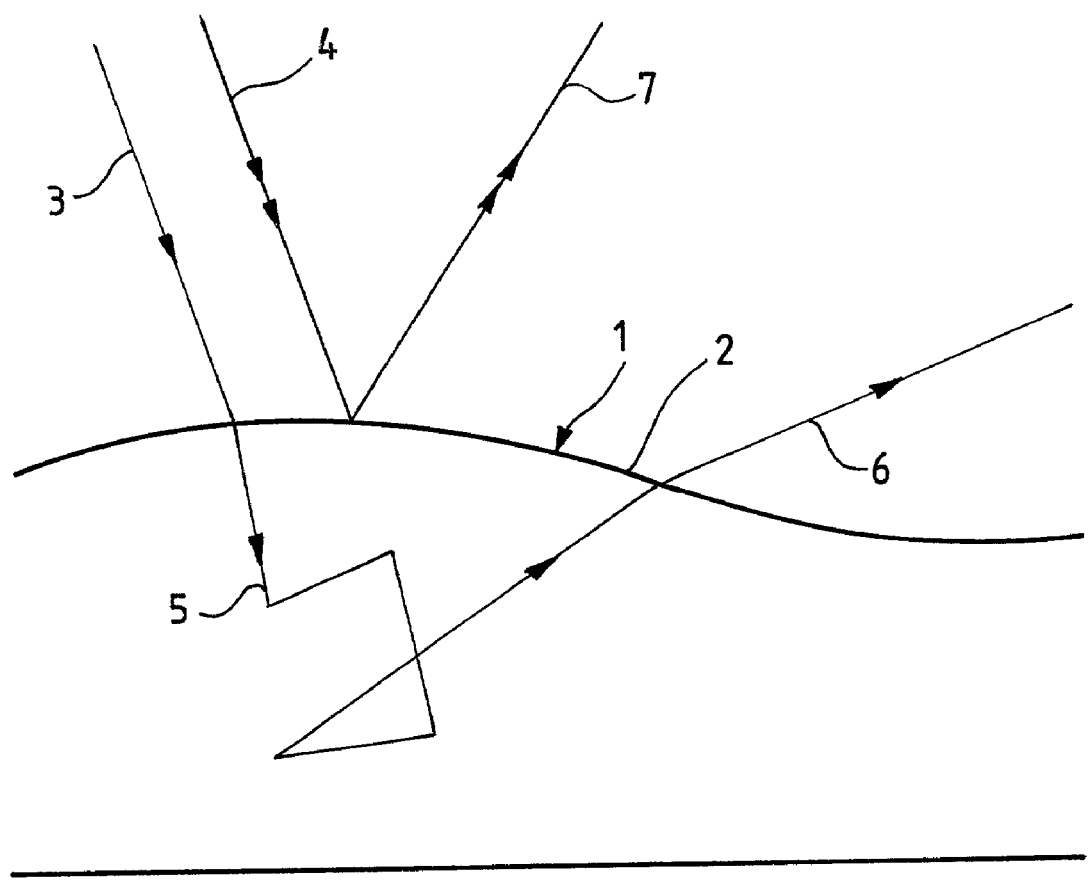
FIG_1

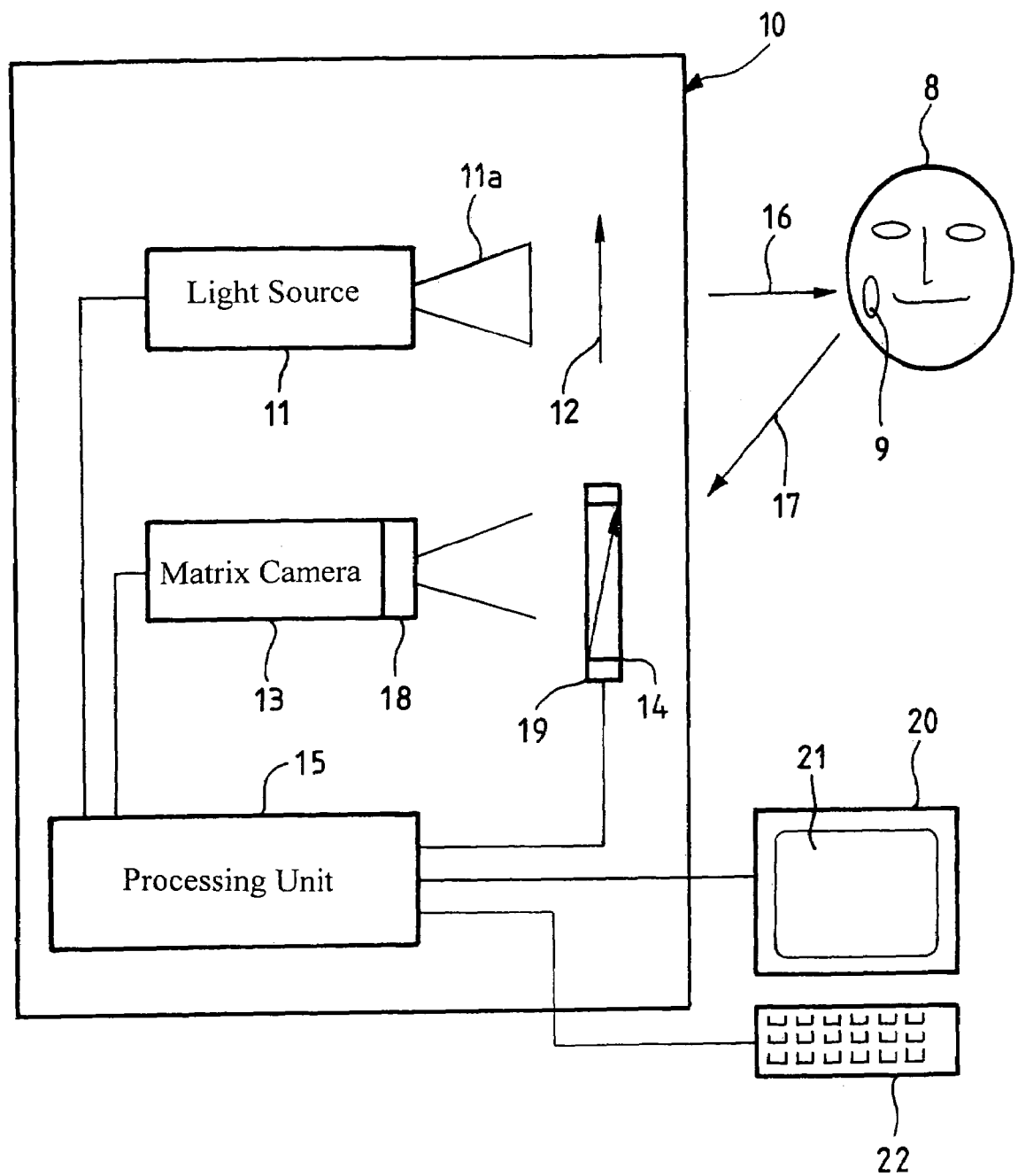

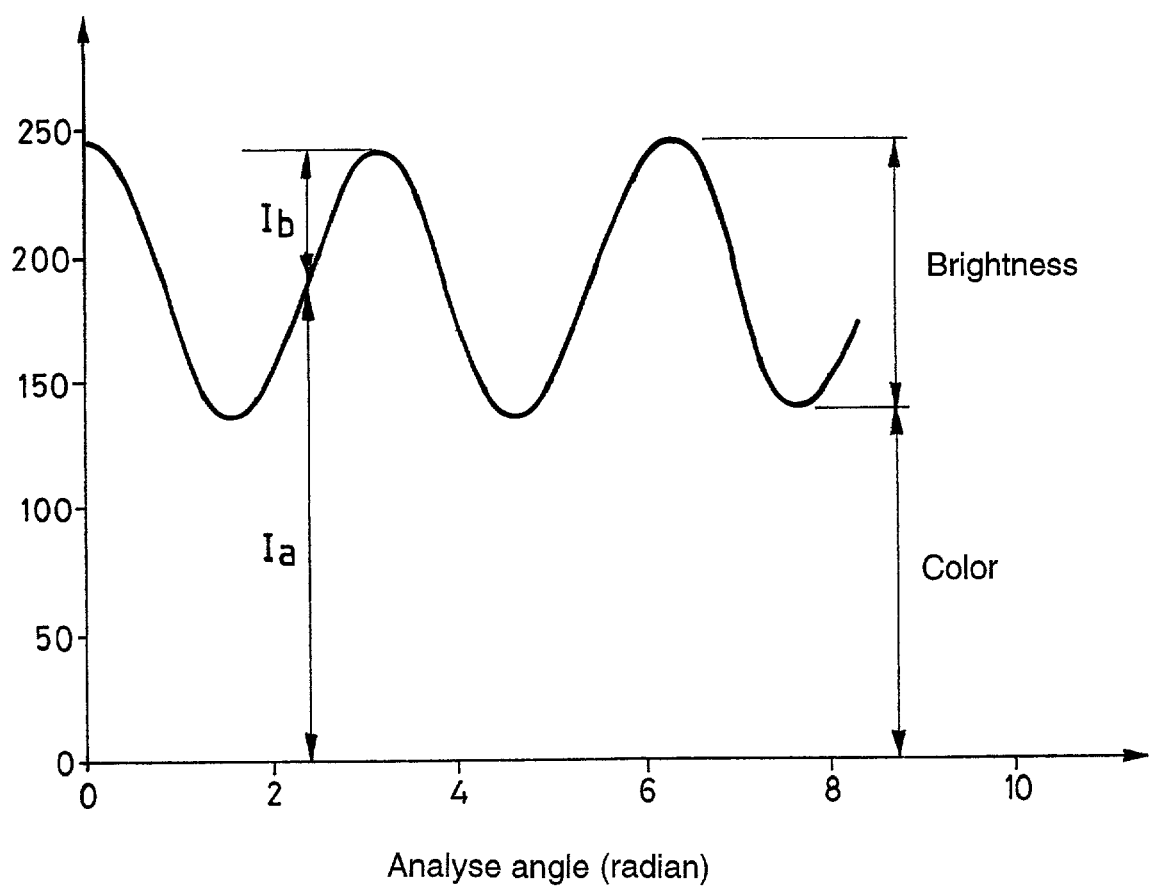
FIG_3

FIG_4
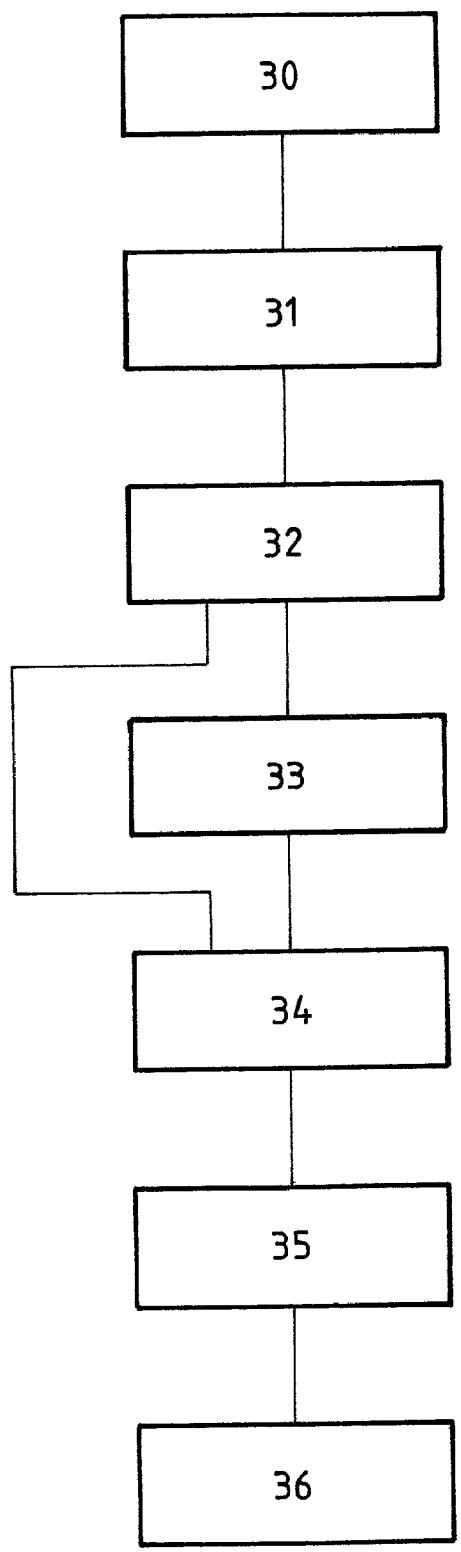

APPARATUS AND PROCESS FOR EXAMINING A SURFACE

FIELD OF THE INVENTION

The invention relates to an apparatus and to a process designed to make it possible to evaluate the characteristics of a surface, in particular the brightness, for example of the skin or more generally of all keratinous surfaces.

BACKGROUND OF THE INVENTION

The apparatus is of the kind comprising a light source directed towards the surface to be examined, a photodetector means sensitive to the light reflected by the surface, means to measure the specular reflection and the diffuse reflection from the surface and means to determine the brightness from the measurement of the specular reflection and of the diffuse reflection. On this subject, document FR-A-2 650 890 can be consulted. The tests carried out have shown that such an apparatus, while giving satisfactory results, has a relatively small sensitivity and discriminative power.

Document EP B 0 475 803 also discloses an apparatus designed to examine a surface, comprising a source of light capable of emitting a beam incident on the surface to be examined, means comprising a polarizer and at least one analyser making it possible to measure the reflection either with the directions of the polarizer and the analyser oriented in parallel, or oriented at right angles, the polarizer being placed between the light source and the surface, while the analyser is placed in the path of the reflected beam, photodetector means sensitive to the light reflected by the surface being, in addition, provided. The light source is directional and the polarized incident beam falls on the surface to be studied at an angle of incidence of between 0 and 90°, limits excluded, the direction of polarization of the incident beam being perpendicular to the plane of incidence. The apparatus is arranged in order to measure the reflection along at least two different reflection directions, one substantially symmetrical with the incident direction relative to the normal to the surface. The apparatus comprises means making it possible to differentiate, for each reflection direction, between the reflection in parallel polarization and analysis directions and the reflection with perpendicular polarization and analysis directions, the differences thus obtained forming a measurement of the so-called specular brightness and of the so-called diffuse brightness.

Such an apparatus functions properly, but only allows the examination of an elementary surface or of a point at a given instant.

SUMMARY OF THE INVENTION

The invention proposes to supply brightness data relating to all the points of a surface at a given instant.

The invention proposes to supply an improved apparatus for surface examination.

According to one aspect of the invention, the apparatus is designed to examine a surface and comprises a polarization analyser element or analyser placed in the path of a light beam reflected by the said surface. In addition, the apparatus comprises a means for taking digital images placed in the path of the beam reflected by the said surface downstream of the analyser, and a processing unit capable of calculating the brightness and the intensity of a plurality of points of the said surface from the pixels of at least two images of the said surface.

The examination can be carried out at some distance from the skin. Thus the risk of altering the characteristics that it is desired to measure is avoided.

The said two images will be taken for different polarizations.

Preferably, the apparatus comprises a source of polarized light capable of emitting a beam incident on the said surface to be examined.

Preferably, the light emanating from the said source is substantially isotropic.

In one embodiment of the invention, the light emanating from the said source is substantially white.

In one embodiment of the invention, the spectrum of the light emanating from the said source is substantially the same as the solar spectrum.

In one embodiment of the invention, the analyser comprises a means for transmitting the crossed polarization and a means for transmitting the parallel polarization, the said transmission means being alternatively active.

In one embodiment of the invention, the analyser is rotating.

In another embodiment of the invention, the analyser comprises an electrical switching means.

The means for taking digital images may be sensitive to colour.

Advantageously, the processing unit will comprise a microprocessor, storage means and software stored in the storage means.

The invention also relates to a process for the examination of a surface, in which the polarization of a light beam reflected by the said surface is analysed, digital images of particular polarizations of the said reflected beam are taken, and the brightness and the intensity of a plurality of points of the image are calculated from the pixels of at least two images of the said surface.

In one embodiment of the invention, the said surface is uneven.

In one embodiment of the invention, monochromatic digital images are taken.

In one embodiment of the invention, polychromatic digital images are taken.

The invention also relates to a computer program comprising program code means to implement the deployment steps of the device, when the said program runs on a computer.

The invention also relates to a storage medium that can be read by a device for reading program code means which are stored thereon and which are capable of implementing the deployment steps of the device, when the said program runs on a computer.

Here, the term point refers to an elementary part of the said surface to be examined, of dimensions corresponding to one pixel of the image obtained by the means for taking images.

In other words, the surface to be examined, which may be a nail or a part of a nail, the face or a part of the face, etc., of a person, is illuminated. The illumination is carried out by a light source or by a plurality of light sources, such that the said illumination is as isotropic as possible. The light emanating from the illumination means is polarized, for example by means of a fixed polarizer. The polarization of the light reflected by the surface to be examined is analysed such that the part of the light whose polarization has been preserved and the part of the light whose polarization has changed are separated, and this for the whole surface to be examined.

Digital images are taken downstream of the analyser, for example by means of a matrix camera, in order to calculate the degree of polarization of each image pixel. From this, information relating to the brightness of the image is deduced by digital processing. To this end, at least two images and preferably three images, in particular for a rotating analyser and an uneven surface, are taken. The examination is done without contact, in order to increase the comfort of the person, one surface of whom is examined, to remove the risk of inaccuracy or of error connected to an alteration of the concave or convex shape of the surface because of contact, and to remove the risk of altering the brightness and therefore of measurement error, in particular for a surface having received beforehand a treatment product, of the make-up, dyeing or care type, where contact is capable of altering the surface distribution.

BRIEF DESCRIPTION OF THE DRAWINGS

The present invention will be better understood and other advantages will appear on reading the detailed description of some embodiments taken by way of non-limiting examples and illustrated by the appended drawings, in which:

FIG. 1 is a schematic view of the reflection of two light rays;

FIG. 2 is a schematic view of an apparatus according to one embodiment of the invention;

FIG. 3 is a curve showing the change in intensity of a pixel as a function of the analyser angle; and FIG. 4 is a flowchart of the steps of the process.

DETAILED DESCRIPTION

FIG. 1 illustrates an object 1 provided with a surface 2 which is illuminated by a light, two incident light rays 3 and 4 of which are shown. The light ray 3 passes through the surface 2 and enters the object 1 along a path 5, then leaves in the form of a diffuse reflected ray 6. This diffuse or "colour" reflection corresponds to light which enters the object, is reflected inside it then is re-emitted outward. The characteristics of the reflected ray 6 depend on the object 1. The incident light ray 4 is reflected on the surface 2 in the form of a reflected ray 7. This type of reflection is called specular and is also called brightness. The light due to the brightness has the spectral characteristics of the incident light. The form of the luminance diagram of the reflected ray 7 depends on the roughness of the surface 2.

As can be seen in FIG. 2, it is desired to examine the face 8 of a person, more particularly a surface 9 of the face 8. To this end, an examination apparatus 10 comprising a light source 11, a fixed polarizer 12, a matrix camera 13, an analyser 14 and a processing unit 15 is provided.

The light source 11 is placed such that it illuminates the surface 9. The light emitted will be as isotropic as possible since it is found that the measurement may be sensitive to the angle of incidence of the light rays on the surface 9. In any case, the light source 11 will have to reproduce the solar spectrum as closely as possible, that is to say, to emit white light.

More particularly, the light source 11 comprises a flash or continuous lamp with an extended spectrum of the xenon or fluorescent-tube type or multicolour light-emitting diodes. The light source 11 also comprises an optical system 11a of the reflector, mirror, objective-lens, light-condenser and optical-fibre type, in order to direct the light at a predetermined angle matched to the surface 9.

The fixed polarizer 12 is placed in the path of the incident light beam 16 emitted by the light source 11, in other words, between the light source 11 and the surface 9. Downstream of the fixed polarizer 12, in the direction of propagation of the incident light beam 16, the light is polarized.

The matrix camera 13 may be of the CCD type and is set up to receive the reflected light beam 17 emanating from the surface 9 when the light source 11 is active. The matrix camera 13 may be provided with an adjustable objective lens 18.

The analyser 14 is placed in the path of the reflected beam 17, in other words, between the surface 9 and the matrix camera 13. The analyser 14 can be oriented, with respect to an axis parallel to that of the reflected beam 17, between at least two positions, for example offset by an angle of 90°. In this way, it is possible to separate the part of the light beam 17 emanating from a specular reflection and the part emanating from a diffuse reflection, it being specified that in one of these two positions, the analyser 14 has the same polarization as the fixed polarizer 12. If this is not the case, any subsequent digital processing may give a constant output. The analyser 14 may be an orientable polarizer, advantageously provided with a motor 19 capable of rotating it. The motor 19 may be of the stepper-motor type, with high resolution if possible, in order to provide accurate polarization.

The light source 11, the camera 13 and the motor 19 of the orientable polarizer 14, are connected to the processing unit 15 which is of the type comprising at least one memory, at least one microprocessor and at least one control program stored in a memory and capable of being executed by the microprocessor or microprocessors. The processing unit 15 is capable of controlling the turning on/off of the light source 11, the taking of images by the camera 13 and, if required, the adjustment of the objective lens 18 and the appropriate orientations of the analyser 14.

The processing unit 15 may also be connected to devices external to the examination apparatus 10, for example to a monitor 20 provided with a screen 21 making it possible to display images able to represent either the surface 9, or results of the examination carried out, that is to say, data processed by the processing unit 15. The processing unit 15 may also be connected to a keyboard 22 making it possible for an operator to input information or commands.

The orientable polarizer may be of the type with electrooptical orientation, for example the "polarization rotator" of Displaytech, or with mechanical orientation, for example with a motor and a plurality of filters mounted on a wheel driven by the motor. As a variant, it is also possible to provide a polarizing splitter cube, for example the "beam splitter" of Oriel, but which however would require the use of two measurement cameras. Preferably, the analyser 14 is an electrooptical system which switches in real time and can be synchronized by an external channel connected to the control unit 15. The analyser 14 makes it possible to separate the brightness, which is a component of light reflected in a specular manner by the surface 9, from the colour, which is a component of light backscattered by the surface 9, when the said analyser is placed in front of the matrix camera 13. When the analyser 14 is in the same direction of polarization as the incident light beam 16, the camera 13 picks up the light reflected by the surface 9 together with half of the depolarized component. When the analyser 14 is in a polarization direction orthogonal to the incident light beam 16, the camera 13 picks up only half of the depolarized component. The processing unit 15 carries out the algebraic operation of subtraction in order to obtain the light component linked to the brightness and of multiplication in order to obtain the light component linked to the colour.

Preferably, and for better accuracy, a sufficient number of images are acquired for any positions of the analyser 14. A Fourier analysis of the measured signal, carried out by the processing unit 15, makes it possible to calculate the degree of polarization of the reflected light beam 17 and to extract from this the brightness component together with the colour component of the surface 9.

The objective lens 18 of the camera 13 makes it possible to focus the reflected light beam at a certain solid angle onto a photosensitive element such as a matrix of CCD cells. For each position of the analyser 14, an image is acquired via an image acquisition board associated either with the processing unit 15 or with the camera 13, for example the "IC-PCI" board of Imaging Technology. The image is acquired when the analyser is in a stationary position after having rotated. The acquisition of two images in parallel and cross polarizations is carried out in a few hundreds of milliseconds.

The matrix of CCD cells provides the radiometer function. Where the spectral distribution of the reflected light beam 17 is of interest, for example the spectral density of the brightness for the specular component and the spectral density of the colour for the backscattered component, it is possible to use a spectrometer. The radiometer function and the spectrometer function can be combined within the same apparatus such as a spectroradiometer.

FIG. 3 illustrates a curve showing the pixel intensity on the Y-axis as a function of the analyser angle on the X-axis. So, if the surface to be examined is illuminated by a polarized light beam, the radiation corresponding to the brightness remains polarized while that corresponding to the colour is depolarized. Rotation of the analyser makes it possible to determine the contribution of the brightness and of the colour at each point of the image. When the analyser is rotated, the intensity at a given point varies in a substantially sinusoidal manner. Upon reflection from the surface to be examined, the orientation of the polarization of the reflected part of the light beam corresponding to the brightness rotates by an amount related to the angle between the incident beam and the normal to the surface to be examined at this point.

If the surface to be examined is plane, the angle through which the polarization rotates is the same at each point. It is then enough to take two images at two different angles of the analyser, one corresponding to the maximum, the other to the minimum of the curve of FIG. 3, in order to determine the part due to colour and the brightness part at each point of the image. The angular positions of the analyser can easily be determined automatically since they correspond to a general minimum and maximum of the image.

If the surface to be examined is uneven, a phase shift appears at each point of the image, and it is necessary to use at least three different positions of the analyser.

The intensity at each point can be written $$I = I_a + I_b \cos(2\theta)$$

where $\theta$ is the angle between the analyser and the vertical, $I_a$ is the mean value of the signal I, and $I_b$ is half the difference between the maximum and the minimum of the signal I.

If, for example, three positions regularly spaced by 45° are used, the following is obtained at each point of the image:

The various steps of the process of examining the surface 9 are illustrated in FIG. 4.

$$I_o = I_a + I_b \cos(2\theta_o)$$

$$I_{45} = I_a + I_b \cos\left(2\left(\theta_o + \frac{\pi}{4}\right)\right) = I_a + I_b \cos\left(2\theta_o + \frac{\pi}{2}\right) = I_a - I_b \sin(2\theta_o)$$

$$I_{90} = I_a + I_b \cos\left(2\left(\theta_o + \frac{\pi}{2}\right)\right) = I_a + I_b \cos(2\theta_o + \pi) = I_a - I_b \cos(2\theta_o)$$

so:

$$I_a = \frac{I_o + I_{90}}{2}$$

$$I_b = [(I_{90} - I_a)^2 + (I_{45} - I_a)^2]^{1/2} = \frac{1}{2}[(I_{90} - I_o)^2 + (I_{45} - I_o - I_{90})^2]^{1/2} \text{ but}$$

$$I_{brightness} = 2I_b \text{ and } I_{colour} = 2(I_a - I_b); \text{ therefore;}$$

$$I_{brightness} = [(I_{90} - I_o)^2 + (I_{45} - I_o - I_{90})^2]^{1/2}$$

$$I_{colour} = I_o + I_{90} - [(I_{90} - I_o)^2 + (I_{45} - I_o - I_{90})^2]^{1/2}$$

At step 30, the operator or even the user controls the start of the examination, for example by means of the keyboard 22.

At step 31, the processing unit 15 having received the start command, sends an activation order to the light source 11 which starts to emit the incident light beam 16.

At step 32, the camera 13 takes an image for an angle of the analyser 14 of 0°.

At step 33, the camera 13 takes an image for an angle of the analyser 14 equal to 450 and at step 34, the camera 13 takes an image for an angle of the analyser 14 of 90°. Where the operator considers that the surface to be examined 9 is plane, in particular where it concerns a very small surface, step 33 can be omitted.

At step 35, the processing unit 15 carries out the numeric calculation making it possible to separate the brightness and colour components in the reflected light beam 17, in other words, to obtain a brightness image and a colour image.

At step 36, the result of the processing is displayed on the screen 21, in the form which appears most suitable, curve, graph, diagram, etc.

During steps 35 and 36, the analyser 14 is designed to return to an angle of 0° in order to be ready to start the examination of another surface.

In another embodiment of the invention, the analyser carries out a continuous rotation during which several images are taken by the camera 13. For a given surface to be examined, the more images are taken, the more accurate will be the estimation of the brightness.

During step 35 of processing by the unit 15, the fact that the human eye is sensitive to the contrast between the brightness and the colour more than the brightness alone, is taken into account. By way of example, a black with a given brightness level will seem brighter than a white with the same brightness level. The unit 15 therefore carries out, on the one hand, a calculation making it possible to map the brightness and, on the other hand, a calculation of the brightness compared with the colour. Preferably, information relating to the brightness compared with the colour, which is the most relevant with regard to the impression perceived by the human eye, will be displayed.

Thus, the surface examination apparatus makes it possible to measure the brightness and the relative brightness of all types of surfaces, in particular keratinous surfaces, for example hair, lips, nails, skin, etc.

These various surfaces may have received beforehand various types of treatment products, for example care, dyeing, make-up products, etc. In the case of make-up, the surface examination apparatus makes it possible to estimate the degree of mattness of the surface, especially of the skin, when it is made up.

The invention claimed is:

1. An apparatus for examining a surface, comprising:
   a polarization analyser element placed in a path of a light beam reflected by the surface, the polarization analyser element constructed and arranged to alternately transmit a crossed polarization state and a parallel polarization state;
   a digital image acquisition device disposed in the path of the beam reflected by the surface downstream of the polarization analyser element; and
   a processing unit configured to calculate a brightness and a color of a plurality of points of the surface from pixels of at least two images of the surface;
   wherein the apparatus is constructed and arranged to examine the surface without contacting the surface.

2. An apparatus according to claim 1, further comprising a source of polarized light configured to emit a beam incident on the surface to be examined.

3. An apparatus according to claim 2, wherein the light emanating from the source is substantially isotropic.

4. An apparatus according to claim 2, wherein the light emanating from the source is substantially white.

5. An apparatus according to claim 2, wherein a spectrum of the light emanating from the source is substantially the same as a solar spectrum.

6. An apparatus according to claim 1, wherein the polarization analyser element comprises a first transmitter configured to transmit crossed polarization and a second transmitter configured to transmit parallel polarization, the first and second transmitters being alternatively active.

7. An apparatus according to claim 6, wherein the polarization analyser element is rotatable.

8. An apparatus according to claim 6, the polarization analyser element further comprises an electrical switching component.

9. A process for a non-contact examination of a keratinous surface, comprising:
   (i) analysing crossed and parallel polarizations of a light beam reflected by the surface;
   (ii) taking digital images of the crossed and parallel polarizations of the reflected beam; and
   (iii) calculating a brightness and a color of a plurality of points of the surface from pixels of at least two images of the surface.

10. A process according to claim 9, wherein the surface is uneven.

11. A process according to claim 9, wherein the digital images are monochromatic digital images.

12. A process according to claim 9, wherein the digital images are polychromatic digital images.

13. The process of claim 9, wherein the process is performed by a computer.

14. A computer-readable medium bearing a program code embodied thereon for performing the process of claim 9.

15. An apparatus for examining a surface comprising:
   a source of polarized light constructed and arranged to emit a beam incident on the surface to be examined, a spectrum of the light being substantially the same as a solar spectrum;
   a polarization analyzer element placed in a path of a light beam reflected by the surface;
   a digital image acquisition device disposed in the path of the beam reflected by the surface downstream of the polarization analyzer element; and
   a processing unit configured to calculate a brightness and a color of a plurality of points of the surface from pixels of at least two images of the surface;
   wherein the apparatus is constructed and arranged to examine the surface without contacting the surface.

16. An apparatus for examining a surface comprising:
   an optical element selected from the group consisting of an orientable polarization analyser element and a polarizing splitter cube placed in a path of a light beam reflected by the surface;
   a first and a second camera configured to take digital images, the first and the second camera being placed in the path of the beam reflected by the surface downstream of the polarization analyser element; and
   a processing unit configured to calculate a brightness and a color of a plurality of points of the surface from pixels of at least two images of the surface;
   wherein the apparatus is constructed and arranged to examine the surface without contacting the surface.

17. An apparatus according to claim 16, further comprising a source of polarized light configured to emit a beam incident on the surface to be examined.

18. An apparatus according to claim 17, wherein the light emanating from the source is substantially isotropic.

19. An apparatus according to claim 15 or 17, wherein the light emanating from the source is substantially white.

20. An apparatus according to claim 15 or 17, wherein a spectrum of the light emanating from the source is substantially the same as a solar spectrum.

21. An apparatus according to claim 15 or 16, wherein the polarization analyser comprises a first transmitter configured to transmit the crossed polarization and a second transmitter configured to transmit the parallel polarization, the first and second transmitters being alternatively active.

22. An apparatus according to claim 21, wherein the polarization analyser is rotatable.

23. An apparatus according to claim 21, wherein the polarization analyser further comprises an electrical switching component.

* * * * *